(12) United States Patent
Krupa et al.

(10) Patent No.: US 9,132,213 B2
(45) Date of Patent: Sep. 15, 2015

(54) VACUUM REGULATOR WITH PRE-SET AND CALIBRATION FEATURES

(75) Inventors: Michael A. Krupa, Northampton, PA (US); Michael J. Krupa, Northampton, PA (US)

(73) Assignee: PRECISION MEDICAL, INC., Northampton, PA (US)

( * ) Notice: Subject to any disclaimer, the term of this patent is extended or adjusted under 35 U.S.C. 154(b) by 412 days.

(21) Appl. No.: 13/589,562

(22) Filed: Aug. 20, 2012

(65) Prior Publication Data

US 2014/0052082 A1 Feb. 20, 2014

(51) Int. Cl.
*A61M 1/00* (2006.01)

(52) U.S. Cl.
CPC ........... *A61M 1/0027* (2014.02); *A61M 1/0035* (2014.02); *A61M 1/0049* (2013.01)

(58) Field of Classification Search
USPC .......................................... 603/318; 604/318
See application file for complete search history.

(56) References Cited

U.S. PATENT DOCUMENTS

| | | | | |
|---|---|---|---|---|
| 3,447,380 | A * | 6/1969 | Martin | 73/736 |
| 3,659,605 | A * | 5/1972 | Sielaff | 604/540 |
| 3,812,855 | A * | 5/1974 | Banko | 604/31 |
| 5,599,308 | A | 2/1997 | Krupa | |
| 5,902,267 | A * | 5/1999 | Medo | 604/74 |
| 6,412,187 | B1 * | 7/2002 | Sasaki et al. | 33/784 |
| 6,623,463 | B2 | 9/2003 | Jones et al. | |
| 6,712,799 | B2 * | 3/2004 | Waddell et al. | 604/321 |
| 6,960,190 | B2 * | 11/2005 | Stinson | 604/119 |
| 7,441,460 | B2 * | 10/2008 | Krupa et al. | 73/753 |
| 7,814,932 | B2 * | 10/2010 | Stinson | 137/557 |
| 7,879,228 | B2 * | 2/2011 | Dunn et al. | 210/104 |
| 8,193,944 | B2 * | 6/2012 | Caso et al. | 340/686.6 |
| 8,456,316 | B2 * | 6/2013 | Caso et al. | 340/686.6 |
| 8,555,727 | B2 * | 10/2013 | Neatrour | 73/700 |
| 8,668,682 | B2 * | 3/2014 | Krupa et al. | 604/540 |
| 2001/0035051 | A1 * | 11/2001 | Karlicek | 73/708 |
| 2006/0107748 | A1 * | 5/2006 | Coleman | 73/736 |
| 2008/0105058 | A1 * | 5/2008 | Krupa et al. | 73/753 |
| 2008/0105508 | A1 * | 5/2008 | Arcese | 190/20 |
| 2011/0282326 | A1 | 11/2011 | Krupa | |
| 2012/0035560 | A1 * | 2/2012 | Eddy et al. | 604/313 |
| 2014/0052082 | A1 * | 2/2014 | Krupa et al. | 604/318 |
| 2014/0261704 | A1 * | 9/2014 | Hoogenakker et al. | 137/1 |

OTHER PUBLICATIONS

Ohio Medical Corporation, "Avoiding the Hazards of Inadvertent Administration of High Suction Pressures," Clinical brochure, Document of 4 pages.
Ohio Medical Corporation, "Ohio Medical's Push-To-Set Intermittent and Continuous Vacuum Regulators," p. 1-12 (2011).

\* cited by examiner

*Primary Examiner* — Tatyana Zalukaeva
*Assistant Examiner* — Guy K Townsend
(74) *Attorney, Agent, or Firm* — Akerman LLP; Richard P. Gilly (57) ABSTRACT

The vacuum regulator includes certain components so that the vacuum regulator is able to be pre-set to a desired vacuum. The vacuum regulator has been calibrated so that a desired vacuum can be selected from a range of vacuums, whether the regulator is in the "off" position or the "on" position, and, the desired vacuum results in delivery of a corresponding level of regulated vacuum when the unit is on.

18 Claims, 6 Drawing Sheets

VACUUM REGULATOR WITH PRE-SET AND CALIBRATION FEATURES

FIELD

This disclosure relates to vacuum regulators, and, in particular, vacuum regulators for use in hospital and other healthcare settings.

BACKGROUND

Vacuum regulators are frequently used in a variety of hospital settings. For example, patients may need to be exposed to vacuum suction to remove secretions from the lungs or other locations. Thus, endotracheal suctioning (ETS) is a fairly common procedure performed in patients with artificial airways, and involves, among other protocols, the aspiration of pulmonary secretions from a patient's airways to prevent obstruction.

Depending upon the particular medical procedure, patient condition, or other factors, it is often preferable to control the level of vacuum to which the patient is exposed and to set a maximum limit of such vacuum level.

Vacuum regulators typically used in hospital or other healthcare settings reduce line vacuum from a hospital source to deliver vacuum in a range suitable for use with intended patients, often ranging from 0 to 300 mmHg Examples of such vacuum regulators include Precision Medical Vacuum Regulator Model PM3300 and PM3400. Such vacuum regulators generally include a regulator module coupled to a rotatable knob, and a vacuum gauge pneumatically connected to the vacuum after it has been regulated by the vacuum module. In suction applications where the distal end of the vacuum tube or other part of the system is exposed to the atmosphere, such exposure to atmosphere will generally mean that the reading on the vacuum gauge shows a lower value than the maximum vacuum level to which the patient could be subjected, such as when secretions are being pulled through the system rather than atmospheric air. Accordingly, in order to determine the maximum vacuum level delivered by typical vacuum regulators, it is generally necessary to fully occlude the outlet of such regulator and make note of the corresponding gauge reading, which reading corresponds to the maximum vacuum to which the patient is exposed. When it is desirable to change the maximum vacuum level from one limit value to another limit value, a similar occlusion procedure is generally followed, in which the occluded regulator is adjusted by means of the rotating knob from one vacuum level indicated by the gauge to another vacuum level indicated by the gauge.

Without fully occluding the vacuum regulator, it may be a challenge for the healthcare provider to accurately gauge the level of vacuum to which the patient will be subjected. This could mean less optimal treatment of the patient, either because the vacuum is too low to be effective or too high and thus inappropriate for applicable procedure. It may be especially challenging to know the level of vacuum to which the patient is subjected when the unit is first turned on.

Furthermore, if there are vacuum collection canisters, trap bottles, or other elements in the corresponding vacuum system which are leaking or otherwise inadvertently open to the atmosphere, and if the occlusion test is performed so that such leaking components are between the regulator and the occluded end of the vacuum system, it is possible that the corresponding gauge reading, under the current art, will be lower than the maximum vacuum to which the patient could be subject if the intervening components were sealed from leaks or exposure to the atmosphere.

Accordingly, it would be desirable to overcome these and other aspects of current vacuum regulators in terms of delivering a desired vacuum level in a hospital or other healthcare setting.

SUMMARY

According to one implementation, a vacuum regulator is adapted for delivering vacuum from a vacuum source for use in conjunction with a patient. The vacuum regulator includes a vacuum mode switch which can be operated between an "off" position and one or more "on" positions. A mechanism can be operated to pre-set the level of vacuum to be delivered from the vacuum regulator to a predetermined value. The mechanism can be operated when the vacuum mode switch is in the "off" position and results in the indicated vacuum being delivered when the vacuum regulator is turned to one of its "on" positions. The mechanism may comprise an adjustable vacuum level selector and a regulator module which is connected to the vacuum level selector. The regulator module in the vacuum regulator has been calibrated to deliver a level of vacuum which corresponds to the desired value indicated by the vacuum level selector.

According to another implementation, a vacuum regulator has a vacuum circuit defined therein, this circuit delivering vacuum to a patient and having an inlet portion which is pneumatically connected to the source of vacuum, and an outlet portion adapted to deliver vacuum from the regulator for use in conjunction with a patient. A regulator module is in pneumatic communication with the vacuum circuit and is adjustable to regulate the vacuum from a vacuum source in order to deliver regulated vacuum to a patient through an associated vacuum system. In this implementation, the vacuum regulator includes a gauge in pneumatic communication with the vacuum circuit, which measures the pressure of the regulated vacuum. There is also a vacuum level selector which can be operated to select a vacuum pressure from a range of vacuum pressures available for delivery. The vacuum gauge has a display which indicates the pressure of the regulated vacuum, whereas the vacuum level selector is associated with a second display which indicates the value of the desired vacuum pressure to be delivered from the regulator. The vacuum level selector is calibrated to the operation of the regulator module, so that when the vacuum level selector is operated to indicate a desired vacuum pressure, the regulator module is in a position which corresponds to the actual vacuum to be delivered.

The details of one or more embodiments are set forth in the accompanying drawings, and the description below. Other features, objects, and advantages of the implementations described herein will be apparent from the description and drawings, and from the claims.

DESCRIPTION OF DRAWINGS

Like reference symbols in the various drawings indicate like elements.

DETAILED DESCRIPTION

Figure 1:
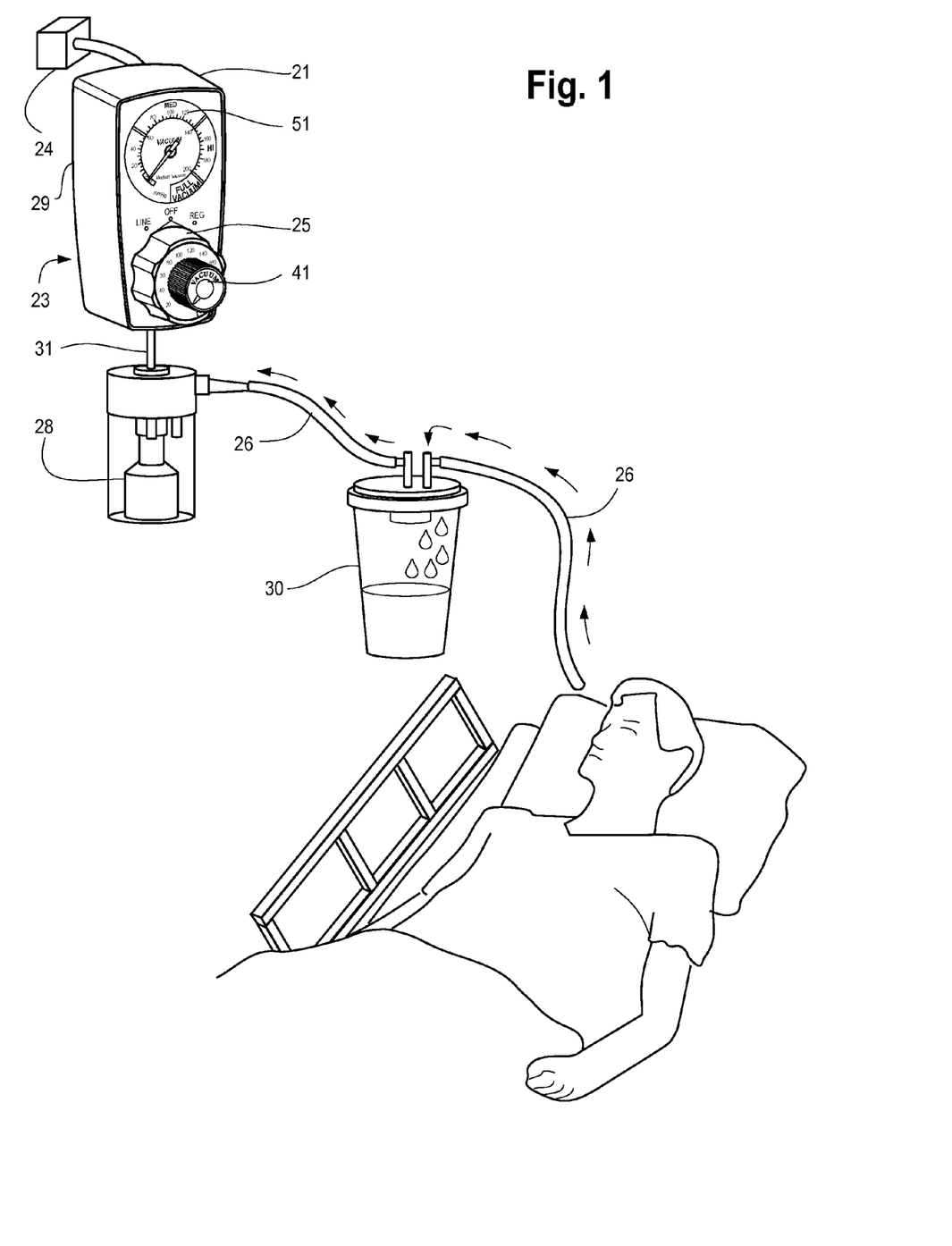
FIG. 1 is a schematic of an exemplary vacuum system according to the present disclosure.

Referring now to the drawings, and in particular to FIG. 1, a vacuum regulator 21 is shown as part of a vacuum system 23. In this implementation, vacuum system 23 is part of a hospital or other patient care facility and associated with patients in such facility. As such, vacuum regulator 21 has an inlet 29 which is adapted to be in pneumatic communication with a source of vacuum 24 associated with vacuum system 23. Vacuum regulator 21 further includes an outlet 31, which is adapted to be placed in pneumatic communication with the patient for any number of purposes, such as for the removal of fluids, or for treating any number of medical or post-operative conditions.

In the arrangement of FIG. 1, which is just one of many possible ones, vacuum system 23 includes a trap bottle 28 to prevent secretions from entering the regulator 21, and a canister 30 to collect patient secretions, pneumatically connected via suitable tubing 26 or other means between regulator 21 and the patient. The hospital vacuum source 24 may be in the range of about 21" Hg, and the regulator 21 reduces such "line" vacuum from source 24 to a vacuum level set by user, in this implementation ranging between 0 and 300 mmHg.

Referring now to FIGS. 2-5, vacuum regulator 21, in this implementation, includes various features, so that the level of vacuum delivered from vacuum regulator 21 can be pre-set to a desired vacuum level while regulator 21 is switched off. These features likewise have been configured so that, while the regulator 21 is in one of its "on" states, the level of vacuum may be set to a different vacuum level by selecting a pre-calibrated vacuum pressure. Vacuum regulator 21, when configured for use with vacuum systems, may assume a variety of different forms, and include a variety of related functions. Furthermore, regulator 21 may be configured to deliver vacuum in any number of vacuum ranges or in different modes, such as continuous, intermittent, pediatric, and any number of other applications. Similarly, regulator 21 may work with unregulated vacuum from a central system or be adapted for use with a regulated vacuum source.

Figure 2:
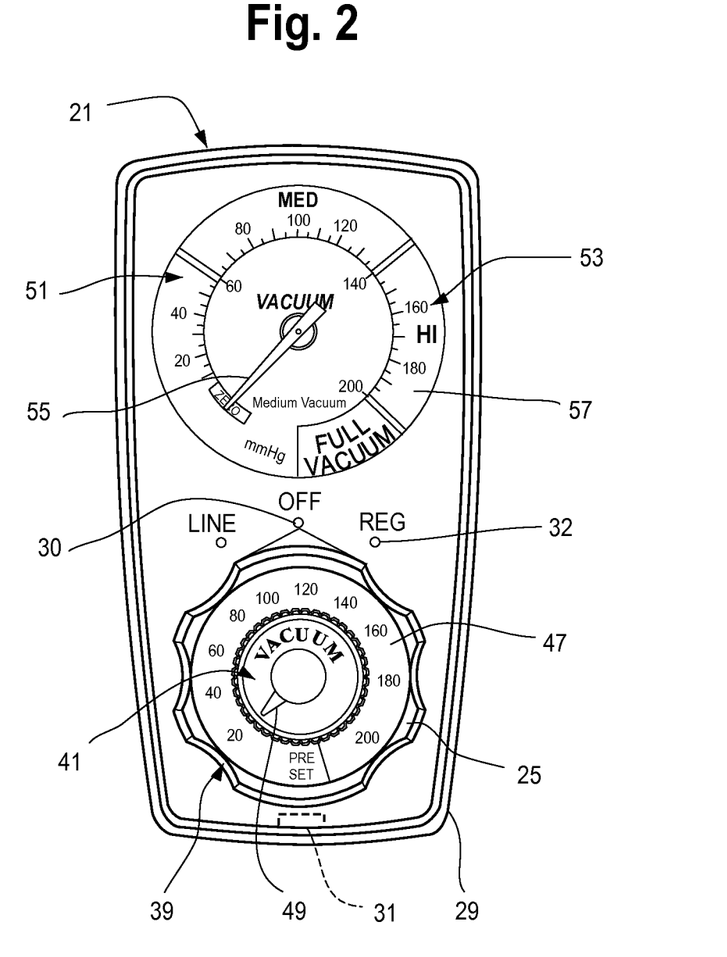
FIG. 2 is a front, elevational view of one implementation of a vacuum regulator according to the present disclosure.
Figure 3:
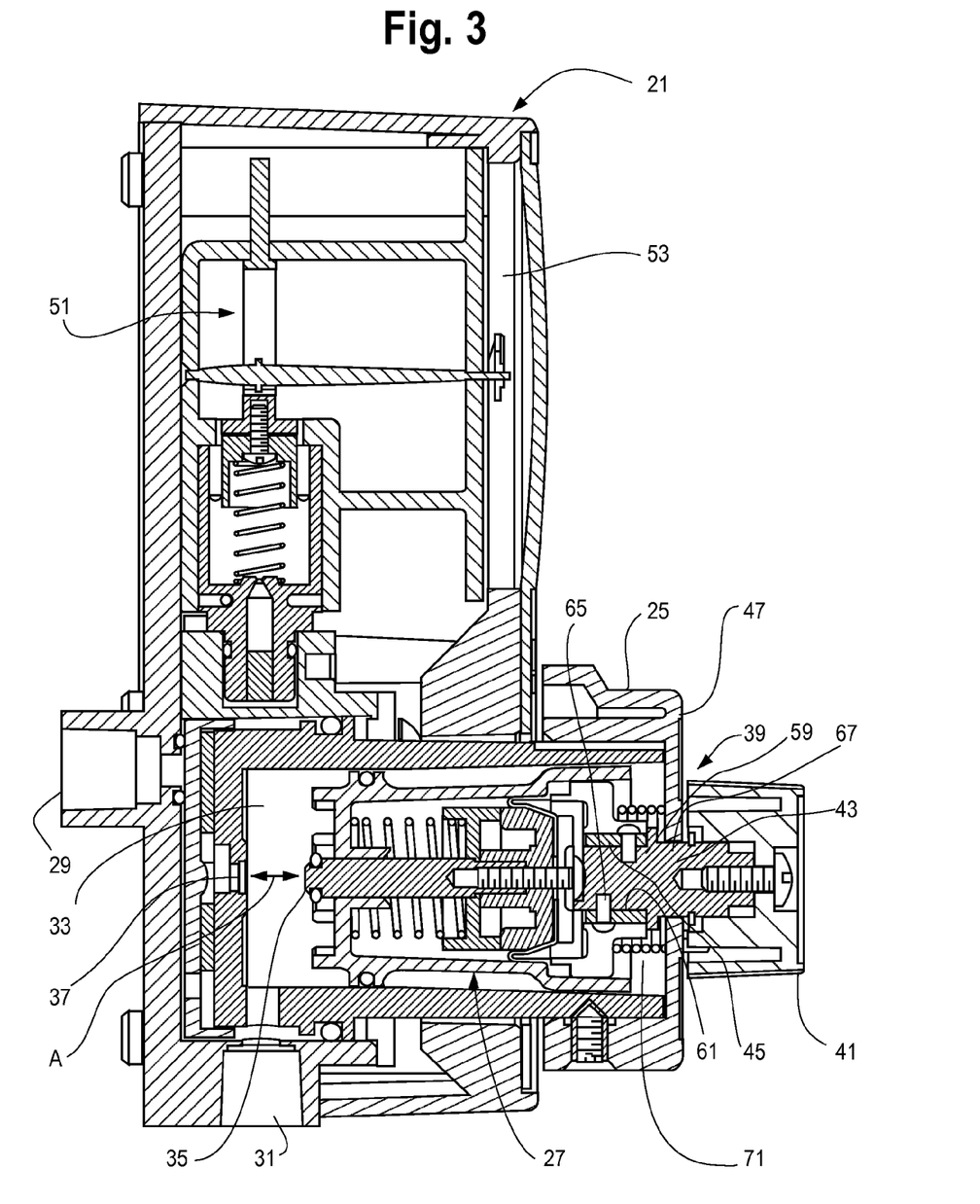
FIG. 3 is a cross-sectional view of the vacuum regulator of FIG. 2.

In any of its various forms, vacuum regulator 21 has a vacuum circuit 33 defined therein. Vacuum circuit extends between inlet 29 and outlet 31. Referring now to FIGS. 1-3, a vacuum mode switch 25 is manually settable to an "off" position 30, in which vacuum is closed off from regulator 21, in this case from inlet 29. Vacuum mode switch 25 is also settable to one or more open or "on" positions 32, in which case inlet 29 is open and vacuum is allowed to enter regulator 21 from the vacuum source.

Figure 4:
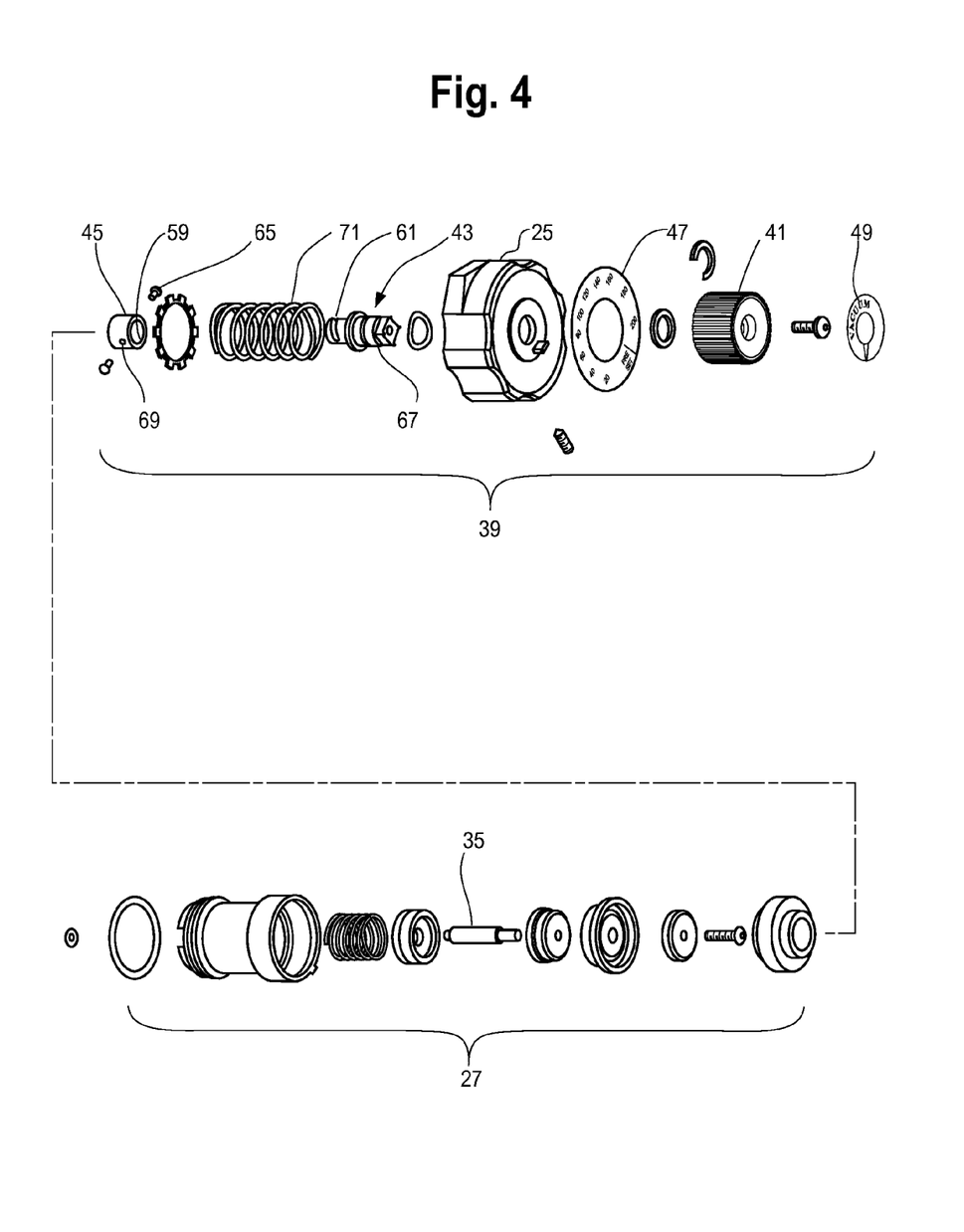
FIG. 4 is an exploded, perspective view of one possible version of pre-set features of the vacuum regulator of FIGS. 2-4.

Regulator 21 includes a regulator module 27 and associated vacuum level selector 39, further shown in an exploded view in FIG. 4. Regulator module 27 is located within regulator 21 so as to be in pneumatic communication with vacuum circuit 33. Regulator module 27 is adjustable to regulate the vacuum from the vacuum source and deliver such regulated vacuum to the balance of the vacuum circuit 33. Regulator module 27, when adjusted, moves regulator module head 35 in a linear direction shown by reference arrows A relative to portions of vacuum circuit 33, in this case an orifice 37 (FIG. 2). The regulated vacuum delivered from regulator 21 may thus be adjusted to a desired vacuum pressure within a range of vacuum pressures available for delivery.

Adjustable vacuum level selector 39 is operatively connected to regulator module 27, so as to permit the aforesaid adjustment of regulator module 27. Vacuum level selector 39 includes a manually adjustable knob 41 and two cooperating elements 43, 45. Cooperating elements 43, 45 are adapted to move relative to each other when knob 41 is adjusted. In addition, cooperating elements 43, 45 are operatively connected to regulator module 27 so that regulator module 27 is moved in the linear direction indicated by arrows A, as discussed previously, upon movement of cooperating elements 43, 45, relative to each other. In this implementation, the operative connection between cooperating elements 43, 45 involves connecting cooperating element 43 to rotatable knob 41, to rotate relative to cooperating element 45, and connecting cooperating element 45 to regulator module 27, and configuring elements 43, 45, as described subsequently, so that rotation of one element relative to the other element adjusts regulator module 27.

A display 47 is configured to indicate the value of the desired vacuum pressure to be delivered from regulator 21. Display 47 is positioned so as to be associated with vacuum level selector 39. More particularly, in this implementation, display 47 is arranged around the circumference of knob 41 of vacuum level selector 39. Knob 41 has an outer or upper circular face on which an indicator 49 has been defined. Indicator 49 rotates upon rotation of knob 41. In this way, vacuum level selector 39 can be operated to indicate a desired vacuum pressure by lining up indicator 49 on knob 41 with a corresponding pressure on display 47. As such, display 47 indicates the value of the desired vacuum pressure sought to be delivered from the regulator 21.

Vacuum level selector 39 is calibrated to the operation of regulator module 27. That is, when vacuum level selector 39 is operated, in this case rotated, to indicate a desired vacuum pressure on display 47, the position of regulator module 27 within vacuum circuit 33 is such that it will result in the delivery of the desired and indicated vacuum pressure from outlet 31 of regulator 21.

Vacuum regulator 21 further includes a gauge 51 in pneumatic communication with vacuum circuit 33 so as to measure the vacuum pressure of the regulated vacuum in circuit 33. To that end, gauge 51 has a suitable gauge display 53 to indicate the regulated pressure measured by gauge 51. Although many variations are possible, in this implementation, display 53 is analog, including a needle 55 movable in relation to a graduated vacuum scale 57 on the face of gauge display 53. One alternate form of gauge 51 would be to make use of a suitable electronic gauge and have gauge display 53 in the form of a corresponding digital gauge. Dual gauges, such as one analog and one electronic or digital gauge, are likewise suitable. Gauge 51 is connected pneumatically so that when regulator 21 is in the "off" position, in which the vacuum from the source is closed off from vacuum circuit 33, gauge 51 reads zero. Conversely, when regulator 21 is switched to one of its "on" positions, whether continuous, line, or intermittent, as the case may be, gauge 51 indicates the vacuum pressure being delivered from vacuum circuit 33 from regulator 21 to the overall vacuum system 23.

Figure 5:
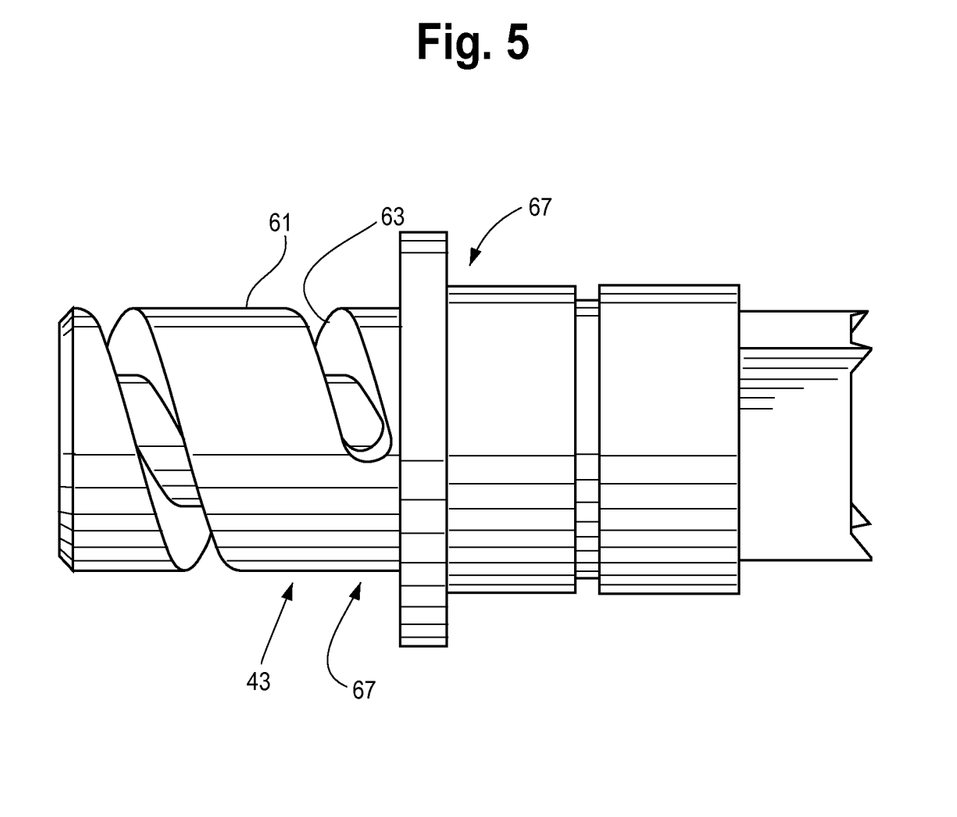
FIG. 5 is a side, elevational view of one of the components of the vacuum regulator of FIGS. 2-4.

As further shown in FIGS. 3-5, cooperating elements 43, 45 include opposing surfaces 59, 61 configured to engage each other. In this implementation, opposing surface 61 includes a spiral groove 63, defined therein, and extending longitudinally along a portion of cooperating element 43. Opposing surface 59 includes at least one pin 65, sized to slidably engage groove 63. Spiral groove 63 may equally be thought of as a spline and pin 65 may assume any number of suitable structural forms or protrusions within its definition, so long as cooperating elements 43, 45 suitably engage each other. Cooperating element 43 is in the form of a barrel 67, the outer surface of which includes opposing surface 61 formed thereon. Cooperating element 45 is in the form of a sleeve 69, which has a circumference suitable to fit around a corresponding portion of barrel 67, as shown in FIG. 4. The inner surface of sleeve 69 includes opposing surface 59, from which pins 65 protrude to engage the spline or spiral groove 63, as discussed previously.

Barrel 67 and sleeve 69 are sized to be rotatable relative to each other and have a common longitudinal axis. Spiral groove 63 is oriented longitudinally, so that barrel 67 and sleeve 69 move relative to each other in a longitudinal direction upon their rotation relative to each other. Sleeve 69 is fixably mounted to regulator module 27 and, by virtue of such connection, rotation of barrel 67 causes regulator module 27 to move in one of the two linear directions shown by reference arrow A. Dial or knob 41 is connected to one of the longitudinal ends of barrel 67 such that rotation of dial or knob 41 results in rotation of barrel 67 relative to sleeve 69. Rotation of knob or dial 41 of vacuum level selector 39 thus results in corresponding rotation of barrel 67 which, in turn, causes pin 65 to move relative to spiral groove 63. Because pins 65 are likewise fixed relative to certain portions of regulator module 27, regulator module 27 is moved linearly in one of the directions of reference arrows A in response to operation of vacuum level selector 39 to select a desired vacuum from the range of vacuums set out on display 47.

While vacuum level selector 39 has been described as including various opposing surfaces 59, 61, as well as cooperating elements 43, 45, and knob 41, and while regulator module 27 has been described to included certain features, it will be appreciated by those skilled in the art that some or all of these features and components may be integrated with each other, or secured relative to each other in a different manner, and that such variations remain within the spirit and scope of the disclosed invention. Thus, for example, pins 65 may assume an alternative form, or may be integrated with sleeve 69. Sleeve 69 may likewise be eliminated as a separate element by being integrated within corresponding portions of regulator module 27, or sleeve 69 may be configured in any number of alternative ways. Similarly, barrel 67 and groove 63 may assume any number of alternate configurations. So, for example, groove 63 may be in the form of a radially extending thread, or barrel 67 may be integral with knob 41. Knob 41, in turn, can be adapted or configured to move in any number of ways relative to display 47.

More generally, the present disclosure contemplates that barrel 67 and sleeve 69 are just one possible implementation of cooperating elements 43, 45. Such cooperating elements 43, 45 may be, alternately, a single component adapted to transfer rotation of knob 41 into calibrated movement of regulator module 27 to effect delivery of the indicated vacuum pressure, or cooperating elements 43, 45 may be features of vacuum level selector 39 and regulator module 27, respectively, and such features may be integral therewith.

Figure 6:
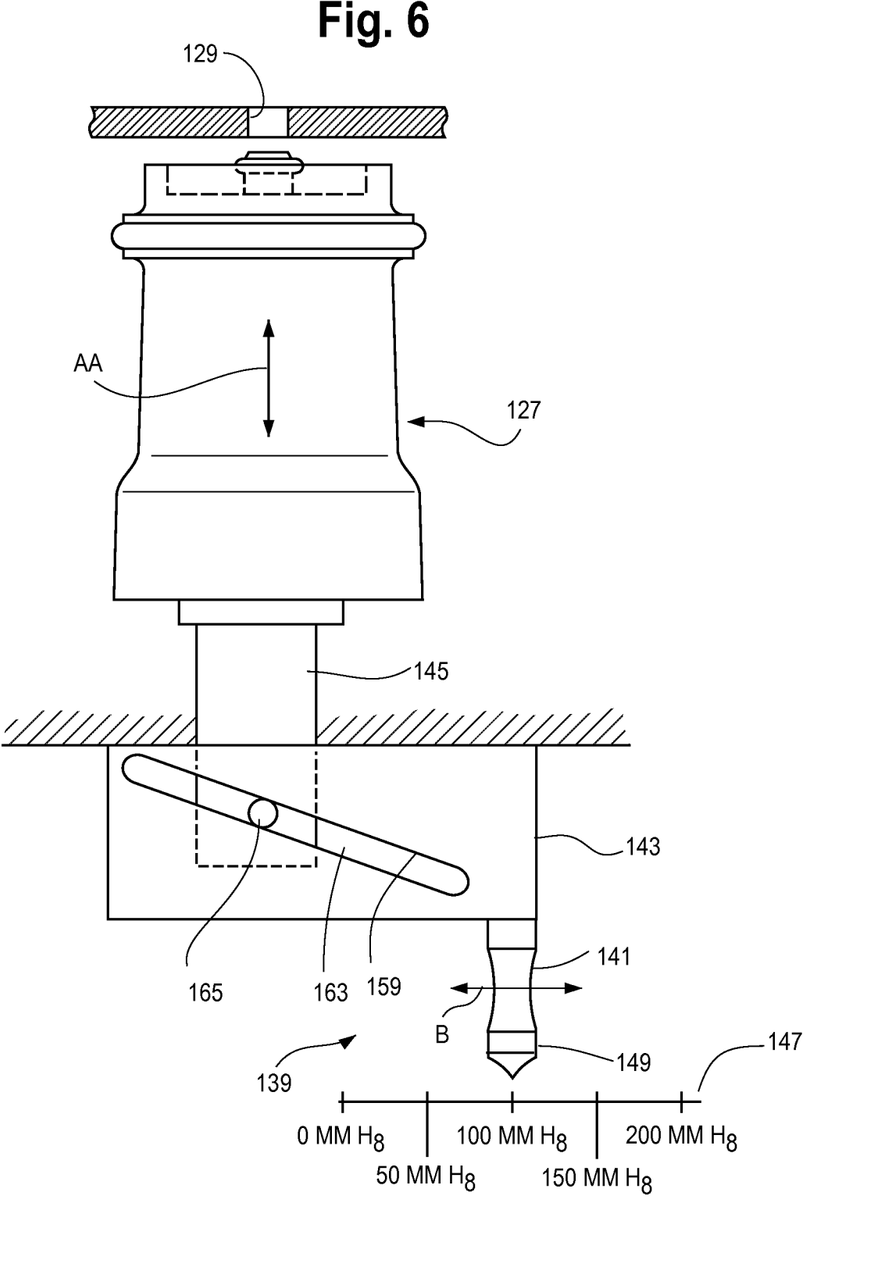
FIG. 6 is a schematic of one possible alternative implementation of certain features of the disclosed vacuum regulator.

So, for example, FIG. 6 is a schematic of one possible alternative implementation of certain features of the disclosed regulator. In particular, the features of one possible alternative implementation of vacuum level selector 139 and regulator module 127 are shown. Vacuum level selector 139 includes a knob 141 manually movable in a back and forth linear direction indicated by the arrows B. Sliding knob 141 includes a suitable indicator 149 which moves relative to a linear display 147 showing a range of available vacuums from zero mm Hg to 200 mm Hg in this implementation. Knob 141, in turn, is either integral or otherwise secured to a first cooperating element 143 which has at least inclined surface 159 defined therein. In this alternative implementation, inclined surface 159 is in the form of a slot 163.

Engaged within slot 163 is a suitable protrusion or pin 165. Pin 165, in turn, is integral or suitably secured to a second cooperating element 145. Cooperating element 145 is integral or suitably secured to regulator module 127. The foregoing arrangement means that the linear movement in the directions B caused by adjustment of knob 141 causes inclined slot 163 to move relative to pin 165. Such relative movement causes pin 165 to engage with one or the other portions of surface 159, such engagement exerting a corresponding linear force which urges cooperating element 145 and regulator module 127 secured thereto in the linear direction indicated by arrows AA.

As in the previous embodiment, the position of regulator module 127 relative to the vacuum inlet 129 is calibrated to the position of indicator 149 relative to vacuum scale 147. In this way, adjustment of knob 141 and its indicator 149, such as by manual movement in the directions of arrows B, will result in a preset or a calibrated selection of a desired level of vacuum from scale 147 indicated by indicator 149.

In view of the foregoing, the functioning of vacuum level selector 139 and regulator module 127 operatively connected thereto proceeds in a manner similar to that discussed above with reference to vacuum level selector 39 and regulator module 27 in the implementation of FIGS. 2-5. Still further variations of all of the foregoing are also contemplated and within the scope of this disclosure.

Regardless of the variation of components used, the operation of vacuum level selector 39 is calibrated to the operation of regulator module 27. In this implementation, calibration is accomplished by determining one or more regulated vacuum pressures corresponding to a position of regulator module 27 relative to vacuum circuit 33, more particularly, the position of regulator module head 35 relative to orifice 37. Vacuum level selector 39 is then calibrated to such determined vacuum level. In this implementation, the vacuum level selector is calibrated to the determined vacuum by positioning knob 41 so that indicator 49 is aligned with the value on display 47 corresponding to the determined vacuum and then secured in such angular position to cooperating element 43 (barrel 67). By virtue of such calibration, the desired vacuum pressure selected by rotation of indicator 49 relative to the vacuum display 47 is produced by vacuum regulator 21 and delivered to outlet 31 and to the upstream elements of vacuum system 23. The calibration is generally effective with an accuracy of ±10 mm Hg. The accuracy of vacuum level selector 39 is further increased by use of a hysteresis spring 71, which exerts a suitable compressive force along the longitudinal axis of vacuum level selector 39 and thus maintains engagement of spiral groove 63 in a consistent manner by pin 65, thereby limited hysteresis between the indicated and desired vacuum pressure produced by the relative position of regulator module 27.

One suitable configuration of vacuum level selector 39 is to advance regulator module 27 in a translational or linear direction by about $250/1000$ of an inch through rotation of knob 41 through about 360° of arc. Spiral groove 63 is defined on the outer surface of barrel 67 to implement such design. Equally suitably, knob 41 may be rotated through about 320° of arc from its zero position to 200 mmHg. Other variations are, of course, possible.

Operation of the vacuum regulator disclosed herein is apparent from the foregoing description. When regulator 21 is pneumatically connected to a vacuum source, such as through a wall outlet in a hospital, the regulator can be operated to be switched to the "off" position or one or more "on" positions. When regulator 21 is switched off, as shown by the position of vacuum mode switch 25 in FIG. 2, there is no vacuum within vacuum circuit 33. A user of vacuum regulator 21 may wish to pre-set the vacuum level to be delivered to a patient connected to the corresponding vacuum system 23 (FIG. 1). This can be accomplished while vacuum mode switch 25 is in the "off" position by manually adjusting knob 41 so that indicator 49 is moved to an arcuate position corresponding to the desired vacuum to be delivered, as set out on display 47. Adjustment of vacuum level selector 39 is calibrated to move regulator module 27, and, in this implementation, is performed while the unit is switched off and independently of gauge 51 and gauge display 53, which will continue to read zero during such selection. Other implementations may expose gauge 51 to vacuum during certain operations of vacuum level selector 39.

Once the desired vacuum has been selected by vacuum level selector 39, the regulator 21 may be switched to "on" by suitable rotation of vacuum mode switch 25 from its off position (shown in FIG. 2) to one of its on positions, indicated in this implementation by the indicia, "REG." (The "line" setting is a bypass feature not associated with the pre-set features of the current disclosure.)

Once regulator 21 has been turned on, vacuum is generally delivered from regulator 21 to the balance of system 23 and ultimately to a patient or other user of such vacuum. Since there are hoses, collection receptacles, and other components to vacuum system 23, located between regulator 21 and the patient, there is an opportunity for leaks to arise in vacuum system 23. Accordingly, the effective vacuum of system 23 may vary from the desired vacuum level indicated by vacuum level selector 39. Thus, for example, if there are leaks in the system, gauge display 53 may indicate a vacuum level which is lower than that selected by vacuum level selector 39. In other words, a difference between the vacuum shown by indicator 49 and the vacuum shown by gauge display 53 may indicate a leak in system 23. Accordingly, the potential for differences between the reading of gauge display 53, and the indicator 49 of vacuum level selector display 47 may be used as a diagnostic tool for those administering the vacuum to assure the integrity of system 23.

Hospital personnel may assess such differences in readings by occluding the distal end of system 23. Occlusion would normally result in a substantial match between gauge 51 and vacuum level selector 39 when there are few or no losses to atmosphere, and conversely, would produce a mismatch in the event of leaks or atmospheric losses.

When the vacuum regulator 21 is delivering vacuum at a desired vacuum level, vacuum level selector 39 may be operated to select a different vacuum level for delivery from regulator 21. This is readily accomplished by manually changing the position of indicator 49 from its current setting to the new desired vacuum level, whether higher or lower. Because vacuum level selector 39 has been calibrated, rotation of knob 41 to the corresponding vacuum pressure has the advantage of increasing the certainty that a vacuum level corresponding to the desired vacuum will, in fact, be delivered when the indicator has been rotated to a desired setting. The vacuum level selector 39 and the user operation thereof can thus be performed independently of the actual vacuum reading of gauge 51 and its corresponding gauge display 53.

Vacuum system 31 may be at least partially exposed to atmosphere in the course of certain treatments, and to a sufficient extent such that gauge 51 periodically or even generally reads lower than the maximum level of vacuum delivered from regulator 21. In such applications, then, the user may use vacuum level selector 39 to set the desired level through indicator 49, such level in these instances corresponding to the maximum vacuum level to which the patient would be exposed, regardless of how much air is entering system 23, and likewise regardless of the corresponding reading of vacuum gauge 51. As such, the calibration of vacuum regulator module 27 and corresponding display 47 permits more certain maximum vacuum limits to be set for a patient even in the face of varying readings of gauge 51. Under certain circumstances, the calibrated nature of vacuum regulator module 27 permits more accurate adjustment of vacuum levels, without needing to occlude the system.

As a further advantage, adjustment from one vacuum level to another vacuum level is accomplished without interrupting the delivery of vacuum from the regulator.

While vacuum regulator 21 in the illustrated implementation is of the continuous type, it will be appreciated that the foregoing disclosure is equally applicable to other types of vacuum regulators, including, without limitation, intermittent, continuous-intermittent, and other vacuum regulators for specialized medical uses with any number of vacuum ranges associated therewith.

A number of embodiments have been described. Nevertheless, it will be understood that various modifications may be made without departing from the spirit and scope of this disclosure. Accordingly, these and other embodiments are within the scope of the following claims

What is claimed is:

1. A vacuum regulator for use in a vacuum system having a vacuum source, the vacuum system associated with a patient, the regulator comprising:
    a vacuum circuit defined within the regulator for delivering vacuum to a patient, the circuit having two ends, an inlet portion at one end adapted to be pneumatically connected to the source of vacuum, and an outlet portion at the other end adapted to deliver vacuum from the regulator for further use with the patient;
    a vacuum mode switch for the regulator, the vacuum mode switch being settable to an "off" position corresponding to closing vacuum off from the regulator, the vacuum mode switch also settable to open the inlet to allow vacuum from the vacuum source into the regulator;
    a regulator module in pneumatic communication with the vacuum circuit, the regulator module being adjustable to regulate the vacuum from the vacuum source to deliver regulated vacuum to the vacuum system, the regulated vacuum having a vacuum pressure within a range of vacuum pressures available for delivery;
    wherein the vacuum mode switch is configured to prevent vacuum from entering the regulator module when the switch is in the "off" position;
    wherein the regulator module includes a regulator head and an orifice in pneumatic communication with the vacuum source, the head being moveable over a range of positions relative to the orifice, the positions being calibrated relative to the vacuum source to correspond to pre-determined levels of vacuum to be selected for delivery;
    wherein the head is configured to be moveable to one of the positions to correspond to a selected vacuum;
    wherein the head is configured to be moveable when the vacuum mode switch is in the "off" position, whereby the selected vacuum can be preset when the vacuum mode switch is in the "off" position;

a gauge in pneumatic communication with the vacuum circuit and adapted to measure the pressure of the selected vacuum;

a first display associated with the gauge and adapted to indicate the pressure of the selected vacuum measured by the gauge;

a vacuum level selector connected to the regulator head and operable to move the regulator head over the range of positions to the selected vacuum; and a second display associated with the vacuum level selector and adapted to indicate the value of the selected vacuum;

whereby when the vacuum level selector is operated to indicate the selected vacuum, the regulator head is in a position corresponding to the selected vacuum.

2. The vacuum regulator of claim 1, wherein, when the vacuum mode switch has opened the inlet to receive vacuum from the vacuum source at a first vacuum pressure, the vacuum level selector is operable to select a second vacuum pressure and indicate the second vacuum pressure on the second display.

3. The vacuum regulator of claim 1,
wherein the vacuum level selector and the second display associated therewith are operable independently of the vacuum circuit; and
wherein the vacuum gauge and first display are in pneumatic communication with the vacuum system associated with the patient, whereby differences between the value of the pressures of the regulated vacuum and the desired vacuum indicated on the first and second displays, respectively, may indicate vacuum leaks.

4. The vacuum regulator of claim 1, wherein the vacuum level selector includes two cooperating elements adapted to move relative to each other when the vacuum level selector is operated to select a desired vacuum, the two cooperating elements operatively connected to the regulator module to move the regulator module upon movement of the cooperating elements relative to each other.

5. The vacuum regulator of claim 4, wherein the two cooperating elements include first and second opposing surfaces configured to engage each other.

6. The vacuum regulator of claim 5, wherein the first opposing surface includes a spiral groove, and the second opposing surface includes at least one pin, the pin sized to engage the groove, the cooperating elements comprising a barrel and a sleeve, the outer surface of the barrel comprising one of the opposing surfaces, the inner surface of the sleeve comprising the other opposing surface, the barrel and the sleeve sized to be rotatable relative to each other and having a common longitudinal axis, the spiral groove oriented to move the barrel and the sleeve longitudinally relative to each other upon rotation.

7. The vacuum regulator of claim 6, wherein the vacuum level selector includes an indicator and a vacuum scale rotatable relative to each other.

8. The vacuum regulator of claim 7, wherein the indicator is formed on a dial and the scale comprises an arcuate band of desired vacuums adjacent to the dial, the dial being rotatable to indicate one of the desired vacuums, the dial being connected to one of the barrel and the sleeve to transmit rotation of the dial into rotation of the barrel and the sleeve relative to each other.

9. The regulator of claim 1, wherein the second display includes an indicator and a vacuum scale rotatable relative to each other.

10. A vacuum regulator for delivering vacuum from a vacuum source for use by a patient, the regulator comprising:

a vacuum mode switch operable between at least two positions, including at least one vacuum "on" position in which vacuum enters the regulator from the vacuum source, and a vacuum "off" position in which the vacuum source is cut off from the regulator;

a mechanism having a portion in pneumatic communication with the vacuum source when the vacuum mode switch is in one of the "on" positions;

the portion being moveable over a range of positions;

the positions being calibrated relative to the vacuum source to correspond to predetermined levels of vacuum to be selected for delivery;

wherein the portion is configured to be moveable to one of the positions to correspond to a selected vacuum;

wherein the portion is configured to be moveable when the vacuum mode switch is in the "off" position, whereby the selected vacuum can be pre-set when the vacuum mode switch is in the "off" position; and a vacuum gauge in pneumatic communication with the selected vacuum when the vacuum mode switch is in one of the vacuum "on" positions, the vacuum gauge having a vacuum display indicating the selected vacuum for delivery from the regulator.

11. The vacuum regulator of claim 10, wherein the mechanism comprises an adjustable vacuum level selector and a regulator module operatively connected to the vacuum level selector, the regulator module movable in response to operation of the vacuum level selector.

12. The vacuum regulator of claim 11, wherein the vacuum level selector includes an indicator and a vacuum scale moveable relative to each other, the level of vacuum to be delivered being set-able to the selected vacuum by the relative movement of the indicator and the scale.

13. The vacuum regulator of claim 11,
wherein, during operation of the regulator in one of the "on" positions, the vacuum level selector is adjustable from a first pre-determined value to a second pre-determined value of vacuum;
wherein, in response to said adjustment, the levels of vacuum being delivered from the regulator are adjusted from the first value to the second value without interruption of vacuum from the regulator.

14. The vacuum regulator of claim 11, wherein the vacuum level selector is manually adjustable.

15. The vacuum regulator of claim 11, wherein the vacuum mode switch is operable between the vacuum "off" position and two vacuum "on" positions, one "on" position corresponding to continuous vacuum, and a second "on" position corresponding to intermittent vacuum.

16. The vacuum regulator of claim 11, wherein the vacuum mode switch is operable between the vacuum "off" position and three vacuum "on" positions, a first "on" position corresponding to continuous vacuum, a second "on" position corresponding to intermittent vacuum, and a third "on" position corresponding to line vacuum.

17. The vacuum regulator of claim 11, wherein the regulator is configured to deliver predetermined levels of vacuum ranging from 0 to 200 mm Hg, through less than 360° of arc to move the portion of the mechanism to a position corresponding to a selected one of the predetermined levels.

18. The vacuum regulator of claim 10, wherein the moveable portion of the mechanism comprises a regulator head in pneumatic communication with the vacuum source through an orifice, the regulator head moveable relative to the orifice.

* * * * *